US009180268B2

(12) United States Patent
Wood et al.

(10) Patent No.: US 9,180,268 B2
(45) Date of Patent: Nov. 10, 2015

(54) CUFF PRESSURE MEASUREMENT DEVICE FOR A TRACHEAL TUBE

(75) Inventors: Lockett Wood, Lyons, CO (US); John Burns, Longmont, CO (US); Sarah Hayman, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 756 days.

(21) Appl. No.: 13/461,292

(22) Filed: May 1, 2012

(65) Prior Publication Data

US 2013/0291871 A1    Nov. 7, 2013

(51) Int. Cl.
*A61M 16/04* (2006.01)

(52) U.S. Cl.
CPC ......... *A61M 16/044* (2013.01); *A61M 16/0445* (2014.02); *A61M 2205/3569* (2013.01); *A61M 2205/3592* (2013.01)

(58) Field of Classification Search
CPC ... A61M 13/003; A61M 16/00; A61M 16/04; A61M 16/0402; A61M 16/0409; A61M 16/0427; A61M 16/0434; A61M 16/044; A61M 16/0445; A61M 16/0461; A61M 16/0463; A61M 16/0465; A61M 16/0468; A61M 16/0472; A61M 16/0475; A61M 16/0477; A61M 16/0479; A61M 16/0484; A61M 16/0486; A61M 16/0683; A61M 2025/0002; A61M 2025/0003; A61M 2025/0008; A61M 25/04; A61M 25/10; A61M 25/1018; A61M 25/10181; A61M 25/10184; A61M 25/10187; A61M 25/10188; A61M 25/104; A61M 2025/1059; A61M 29/00; A61M 2205/3341; A61M 2205/3569; A61M 2205/3592; A61M 2205/505; A61M 2205/582; A61M 2205/583; A61M 2205/8212; A61B 1/041; A61B 1/233; A61B 1/267; A61B 1/2676; A61B 5/0031; A61B 5/0215; A61B 5/03; A61B 5/031; A61B 5/037; A61B 5/06; A61B 5/205; A61B 5/42; A61B 5/4233; A61B 17/12022; A61B 17/12104; A61B 17/12099; A61B 17/12131; A61B 17/12136; A61B 2017/22051; A61B 2017/22069; A61J 15/00; A61J 15/0015; A61J 15/003; A61J 15/0046; A61J 15/0049; A61J 15/008; G01L 7/02; G01L 9/0002; G01L 9/0004; G01L 9/0005; Y10S 116/09; Y10T 137/8326
USPC ......................................................... 73/700
See application file for complete search history.

(56) References Cited

U.S. PATENT DOCUMENTS 3,931,822 A    1/1976  Marici
4,134,407 A *  1/1979  Elam ........................ 128/202.22

(Continued)

OTHER PUBLICATIONS

N. Lomholt; "A device for measuring the lateral wall cuff pressure of endotracheal tubes;" Acta Anaesthesiol Scand (1992). vol. 36; pp. 775-778.

(Continued)

*Primary Examiner* — Lynne Anderson
*Assistant Examiner* — Mark K Han
(74) *Attorney, Agent, or Firm* — Fletcher Yoder PC

(57) ABSTRACT

According to various embodiments, methods and systems for determining pressure in an inflatable cuff of a tracheal tube may employ pressure transducers associated with a cuff inflation line or a pilot balloon assembly. The pressure transducers may be implemented to provide continuous or intermittent cuff pressure. Also provided are tracheal tubes with adapters or other devices that incorporate pressure transducers. The tracheal tubes may facilitate wireless cuff pressure monitoring.

10 Claims, 9 Drawing Sheets

(56) References Cited

U.S. PATENT DOCUMENTS

| | | | |
|---|---|---|---|
| 4,266,550 A * | 5/1981 | Bruner | 604/100.01 |
| 4,285,340 A | 8/1981 | Gezari et al. | |
| 4,526,196 A | 7/1985 | Pistillo | |
| 4,552,558 A | 11/1985 | Muto | |
| 4,565,194 A | 1/1986 | Weerda et al. | |
| 4,617,015 A | 10/1986 | Foltz | |
| 4,630,606 A | 12/1986 | Weerda et al. | |
| 4,898,168 A | 2/1990 | Yule | |
| 5,218,970 A * | 6/1993 | Turnbull et al. | 600/561 |
| 5,235,973 A | 8/1993 | Levinson | |
| 5,361,753 A | 11/1994 | Pothmann et al. | |
| 5,487,383 A | 1/1996 | Levinson | |
| 5,819,723 A | 10/1998 | Joseph | |
| 6,530,898 B1 | 3/2003 | Nimkar et al. | |
| 6,647,984 B1 | 11/2003 | O'Dea | |
| 7,686,019 B2 | 3/2010 | Weiss et al. | |
| 2009/0120445 A1 * | 5/2009 | Chikashige | 128/207.15 |
| 2010/0113939 A1 * | 5/2010 | Mashimo et al. | 600/470 |
| 2010/0312132 A1 | 12/2010 | Wood et al. | |
| 2011/0030694 A1 * | 2/2011 | Schaner et al. | 128/207.15 |
| 2011/0178419 A1 | 7/2011 | Wood et al. | |
| 2011/0230742 A1 * | 9/2011 | Finneran et al. | 600/364 |

OTHER PUBLICATIONS

R. J. Pollard, et al.; "Endotracheal Tube Location Verified Reliably by Cuff Palpation;" Anesth Analog (1995), vol. 81, pp. 135-138.

J. Valentino, et al.; "Utility of portable chest radiographs as a predictor of endotracheal tube cuff pressure;" Otolaryngology—Head and Neck Surgery, Jan. 1999, Vo. 120, No. 1, pp. 51-56.

F. Karasawa et al.; "Profile Soft-Seal Cuff, a New Endotracheal Tube, Effectively Inhibits an Increase in the Cuff Pressure Through High Compliance Rather than Low Diffusion of Nitrous Oxide;" Technology, Computing, and Simulation, Society for Technology in Anesthesia, Anesth Analg (2001), vol. 92, pp. 140-144.

A. Dullenkopf, et al.; "Air leakage around endotracheal tube cuffs;" European Journal of Anesthesiology, (2004), vol. 21, pp. 448-453.

V. Khazin, et al.; "Gastroesophageal regurgitation during anesthesia and controlled ventilation with six airway devices;" Journal of Clinical Anesthesia (2008), vol. 20, pp. 508-513.

D. Graham-Rowe; "Smart contact lenses fo health and head-up displays;" New Scientist Tech, Jan. 10, 2011, pgs. found at http://www.newscientist.com/article/mg20927943.800-smart-contact-lenses.

* cited by examiner

CUFF PRESSURE MEASUREMENT DEVICE FOR A TRACHEAL TUBE

BACKGROUND

The present disclosure relates generally to medical devices and, more particularly, to airway devices, such as tracheal tubes.

This section is intended to introduce the reader to aspects of the art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into the patient. For example, tracheal tubes may be used to control the flow of air or other gases through a patient's trachea and into the lungs, for example during patient ventilation. Such tracheal tubes may include endotracheal (ET) tubes, tracheotomy tubes, or transtracheal tubes. In many instances, it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

To seal these types of tracheal tubes, an inflatable cuff may be associated with the tubes. When inflated, the cuff generally expands into the surrounding trachea (or, in the case of laryngeal masks, over the trachea) to seal the tracheal passage around the tube to facilitate the controlled delivery of gases via a medical device (e.g., through the tube). As many patients are intubated for several days, healthcare workers may need to balance achieving a high-quality tracheal seal with possible patient discomfort. For example, if improperly overinflated, the pressure and/or frictional force of certain types of inflated cuffs against the tracheal walls may result in some tracheal tissue damage. While a cuff may be inflated at lower pressure to avoid such damage, this may lower the quality of the cuff's seal against the trachea. Low cuff inflation pressures may also be associated with allowing folds to form in the walls of the cuff that may serve as leak paths for air as well as microbe-laden secretions.

Additionally, the quality of a cuff's seal against the tracheal passageway may suffer over the duration of a patient's intubation time. For example, a seal may be compromised when a patient coughs, which may dislodge the cuff from a sealed position. Further, when the tracheal tube is jostled during patient transport or medical procedures, the force of the movement may shift the position of the inflatable cuff within the trachea, allowing gaps to form between the cuff and the tracheal walls. Accordingly, it may be desirable to monitor the internal pressure in the cuff to determine if the cuff is properly inflated.

BRIEF DESCRIPTION OF THE DRAWINGS

Advantages of the disclosure may become apparent upon reading the following detailed description and upon reference to the drawings in which.

DETAILED DESCRIPTION OF SPECIFIC EMBODIMENTS

Figure 1:
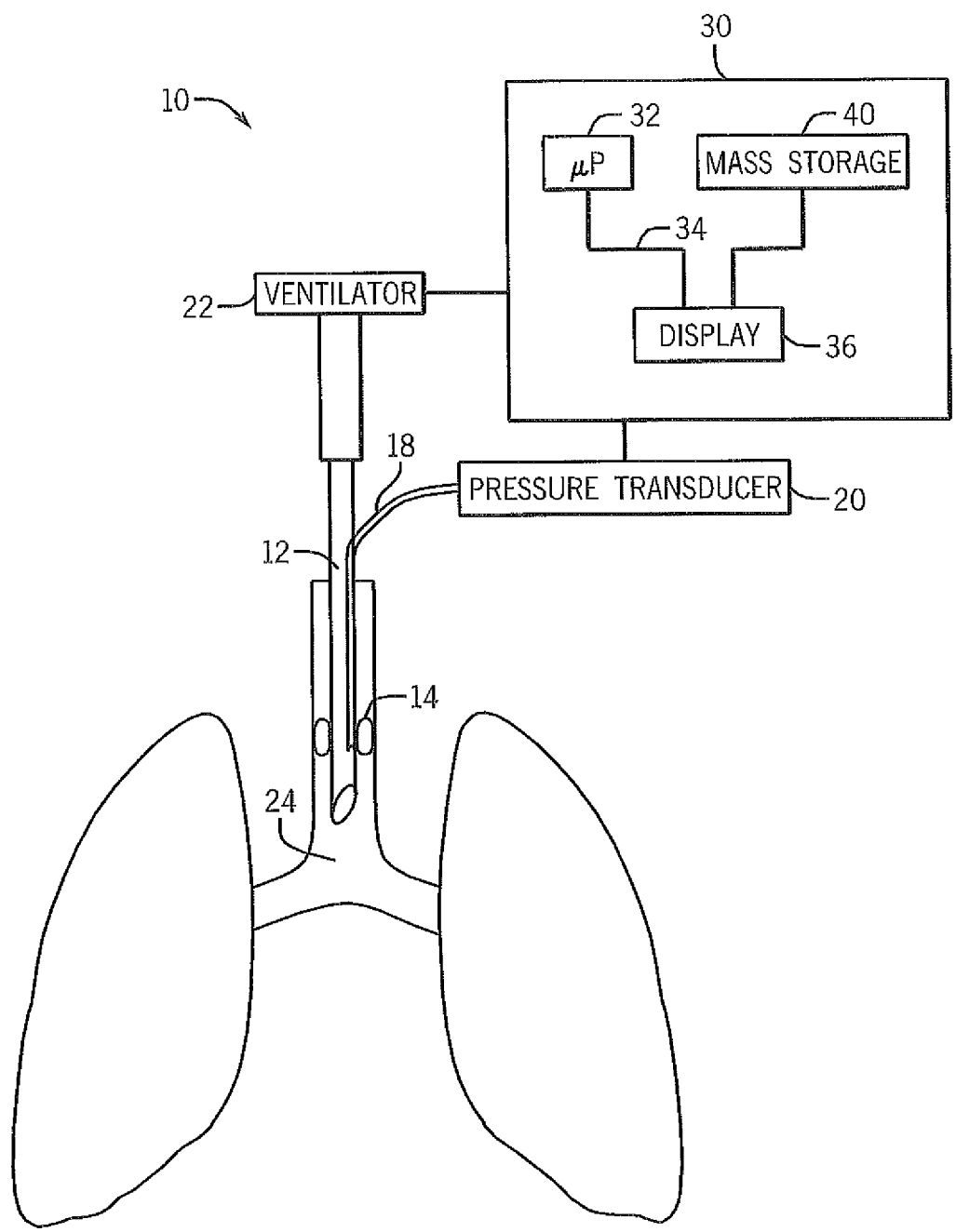
FIG. 1 illustrates a system including a tracheal tube with a pressure transducer for monitoring cuff pressure according to embodiments of the present techniques.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A tracheal tube may be used to seal a patient's airway and provide positive pressure to the lungs when properly inserted into a patient's trachea. A high quality seal of a cuff against the tracheal walls may assist in isolating the lower airway and anchoring the tube in place. However, a conforming seal is often difficult to obtain over long-term intubation. Physicians may attempt to determine the quality of a cuff seal by monitoring inflation pressure via devices such as manometers that are temporarily attached to the exposed valve of the cuff inflation line. However, these devices are generally used intermittently for spot checks of cuff pressure and, therefore, add to the workflow of clinicians. Further, the devices include connecting tubes to transfer gas from the cuff inflation line to pressure sensors. When the devices are disconnected, the air transferred to the devices is lost to the system. Accordingly, each measurement results in an overall decrease in cuff pressure, which may influence the integrity of the cuff seal. Other techniques may involve a qualitative assessment of the stiffness of a pilot balloon associated with the exposed end of the cuff inflation line. However, the pilot balloon stiffness does not provide a quantitative measurement of cuff pressure.

Accordingly, the disclosed embodiments provide a more accurate method and system for determining trachea pressure by obtaining a measurement of pressure with pressure transducers associated with the cuff inflation line or the pilot balloon assembly. Such pressure transducers may include wireless sensors that are capable of communicating with a patient monitor. In particular embodiments, the pressure transducer may include components that are exposed to the interior space of the inflation line system (e.g., including the fluid enclosed by the cuff, the inflation line, and any components in fluid communication the cuff and the inflation line) and components that are exposed to ambient air. In one embodiment, the pressure transducers may be associated with an adapter that is used in conjunction with an inflation line or pilot balloon assembly. For example, a pilot balloon assembly may typically terminate at a proximal end in a valve that opens to allow air to enter or leave the inflation line. As provided herein, an adapter incorporating the valve may include a pressure transducer that is in fluid communication with the pilot balloon and the inflation line. Such an embodiment may provide manufacturing advantages because the tracheal tube, inflation line, and pilot balloon are unchanged. In another embodiment, the pressure transducer may be embedded in or incorporated into a wall of the pilot balloon itself. In yet additional embodiments, a pressure transducer may be incorporated into the inflation line. For example, an in-line adapter may bridge two sections of inflation line and provide a pressure transducer surface that is in fluid communication with the inflation line.

In certain embodiments, the disclosed tracheal tubes, systems, and methods may be used in conjunction with any appropriate medical device, including a tracheal tube, a feeding tube, an endotracheal tube, a tracheotomy tube, a double-lumen tracheal tube (e.g., an endobroncheal tube), a circuit, an airway accessory, a connector, an adapter, a filter, a humidifier, a nebulizer, nasal cannula, or a supraglottal mask/tube. The present techniques may also be used to monitor any patient benefiting from mechanical ventilation, e.g., positive pressure ventilation.

FIG. 1 shows an exemplary tracheal tube system 10 that has been inserted into the trachea of a patient. The system 10 includes a tracheal tube 12, shown here as an endotracheal tube, with an inflatable balloon cuff 14 that may be inflated via inflation line 18 to form a seal against the tracheal walls. The tracheal tube 12 may also include a pressure transducer 20 that is in fluid communication with the cuff 14. In certain embodiments, the pressure transducer 20 may be coupled to a medical device, such as a ventilator 22 or a monitor 30. The monitor 30 and/or the ventilator 22 may be configured to monitor pressure in the cuff 14 and, in particular embodiments, the pressure in the tracheal space 24.

The system 10 may also include devices that facilitate positive pressure ventilation of a patient, such as the ventilator 22, which may include any ventilator, such as those available from Nellcor Puritan Bennett LLC. The system may also include a monitor 30 that may be configured to implement embodiments of the present disclosure to determine pressures based upon the pressure in the cuff 14 or another cuff. It should be understood that the monitor 30 may be a stand-alone device or may, in embodiments, be integrated into a single device with, for example, the ventilator 22.

The monitor 30 may include processing circuitry, such as a microprocessor 32 coupled to an internal bus 34 and a display 36. In an embodiment, the monitor 30 may be configured to communicate with the tube, for example via the pressure transducer 20 or an associated antenna, to obtain signals from the pressure transducer 20. In certain embodiments, the communication may also provide calibration information for the tube 12. The information may then be stored in mass storage device 40, such as RAM, PROM, optical storage devices, flash memory devices, hardware storage devices, magnetic storage devices, or any suitable computer-readable storage medium. The information may be accessed and operated upon according to microprocessor 32 instructions and stored executable instructions. In certain embodiments, calibration information may be used in calculations for estimating of pressure in the cuff based on measurements of pressure in the inflation line or associated structures (e.g., the pilot balloon assembly). The monitor 30 may be configured to provide indications of the cuff pressure, such as an audio, visual or other indication, or may be configured to communicate the estimated cuff pressure to another device, such as the ventilator 22.

Figure 2:
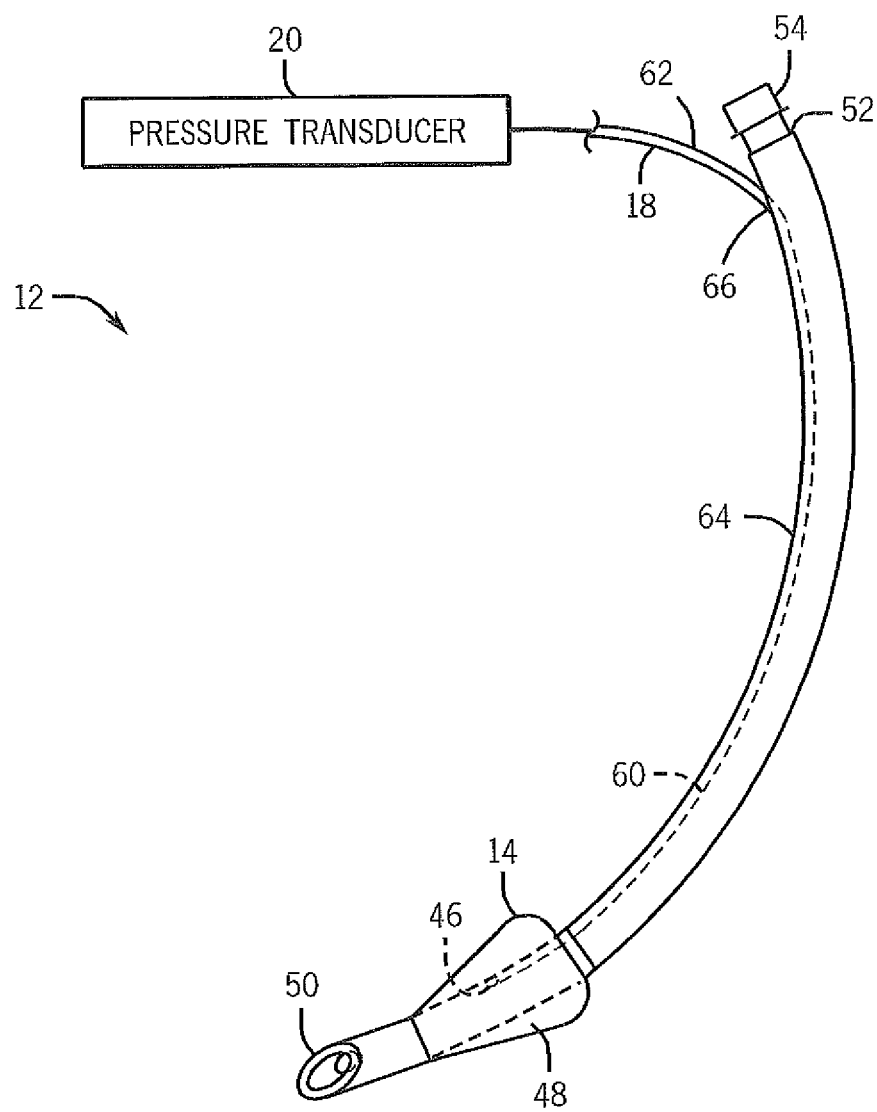
FIG. 2 is a perspective view of an endotracheal tube that may be used in conjunction with the system of FIG. 1.

FIG. 2 is a perspective view of an exemplary tracheal tube 12 according to certain presently contemplated embodiments. It should be understood that the embodiments discussed herein may be implemented with any suitable airway device including a cuff 14, such as a tracheal tube, an endotracheal tube, a tracheostomy tube, a laryngeal mask, etc. Further, the embodiments disclosed herein may be used with any medical device that includes an inflatable component that is inflated via an inflation line that may include a pilot balloon assembly. For example, the tube 12 includes a cuff 14 inflated via inflation lumen 18, which terminates in an opening 46 that is located within the inflated interior space 48 of the cuff 14. The interior space 48 is fluid communication with the pressure transducer 20. The tracheal tube 14 is inserted in the patient such that the distal end 50 and the cuff 14 are positioned within the trachea (see FIG. 1) and the proximal end 52 is located outside of the patient for connection via connector 54 to a ventilator. The inflation lumen 18 includes an interior portion 60 and an exterior portion 62 that extends away from the wall 64 of the tube 12 at an opening 66.

The pressure transducer 20 may be any suitable pressure sensor, such as a piezoelectric pressure sensor. In one embodiment, the pressure sensor may incorporate a passive or active RFID circuit that may be read wirelessly to convey pressure monitoring information and/or calibration or identification information to the monitor 30. In particular embodiments, a passive RFID component without power connections or battery components may be advantageous. The monitor 30 may incorporate an RFID readout device. In one embodiment, the pressure transducer 20 may be part of an assembly that includes a capacitor type pressure sensor and a tuned antenna for a resonance frequency in a medical band, such as a frequency in the 2.450 GHz center frequency or the 5.800 GHz band (or higher). The sensor may be a CMUT (capacitive micromachined ultrasonic transducer) sensor with a movable membrane fabricated onto a silicon chip of a size suitable for the embodiments discussed herein. In certain embodiments, a sweep of the transmission frequency measures the resonant frequency of the pressure transducer 20, which is a function of the cuff pressure. The pressure transducer 20 may be capable of sensing pressures in a range of 0 to 50 cm of $H_2O$.

The pressure transducer 20 may also be associated with an information element, such as a memory circuit, such as an EPROM, EEPROM, coded resistor, or flash memory device for storing calibration information for the pressure transducer 20. The pressure transducer 20 may also be part of an assembly that contains certain processing circuitry for at least partially processing signals from the pressure transducer 20 or for interacting with any memory circuitry provided. When the pressure transducer 20 communicates with the monitor 30, the information element may be accessed to provide calibration information to the monitor 30. In certain embodiments, the calibration information may be provided in a barcode that may be scanned by a reader coupled to the monitor 30. Alternatively, the pressure transducer 20 may include a passive or active RFID circuit that may be read wirelessly to convey pressure monitoring information and cuff calibration information to the monitor 30.

The tube 12 and the cuff 14 are formed from materials having suitable mechanical properties (such as puncture resistance, pin hole resistance, tensile strength), chemical properties (such as biocompatibility). In one embodiment, the walls of the cuff 14 are made of a polyurethane having suitable mechanical and chemical properties. An example of a suitable polyurethane is Dow Pellethane® 2363-80A. In another embodiment, the walls of the cuff 14 are made of a suitable polyvinyl chloride (PVC). In certain embodiments, the cuff 14 may be generally sized and shaped as a high volume, low pressure cuff that may be designed to be inflated to pressures between about 15 cm $H_2O$ and 30 cm $H_2O$. However, it should be understood that the intracuff pressure may be dynamic. Accordingly, the initial inflation pressure of the cuff 14 may change over time or may change with changes in the seal quality or the position of the cuff 14 within the trachea.

The system 10 may also include a respiratory circuit (not shown) connected to the endotracheal tube 12 that allows one-way flow of expired gases away from the patient and one-way flow of inspired gases towards the patient. The respiratory circuit, including the tube 12, may include standard medical tubing made from suitable materials such as polyurethane, polyvinyl chloride (PVC), polyethylene teraphthalate (PETP), low-density polyethylene (LDPE), polypropylene, silicone, neoprene, polytetrafluoroethylene (PTFE), or polyisoprene.

Figure 3:
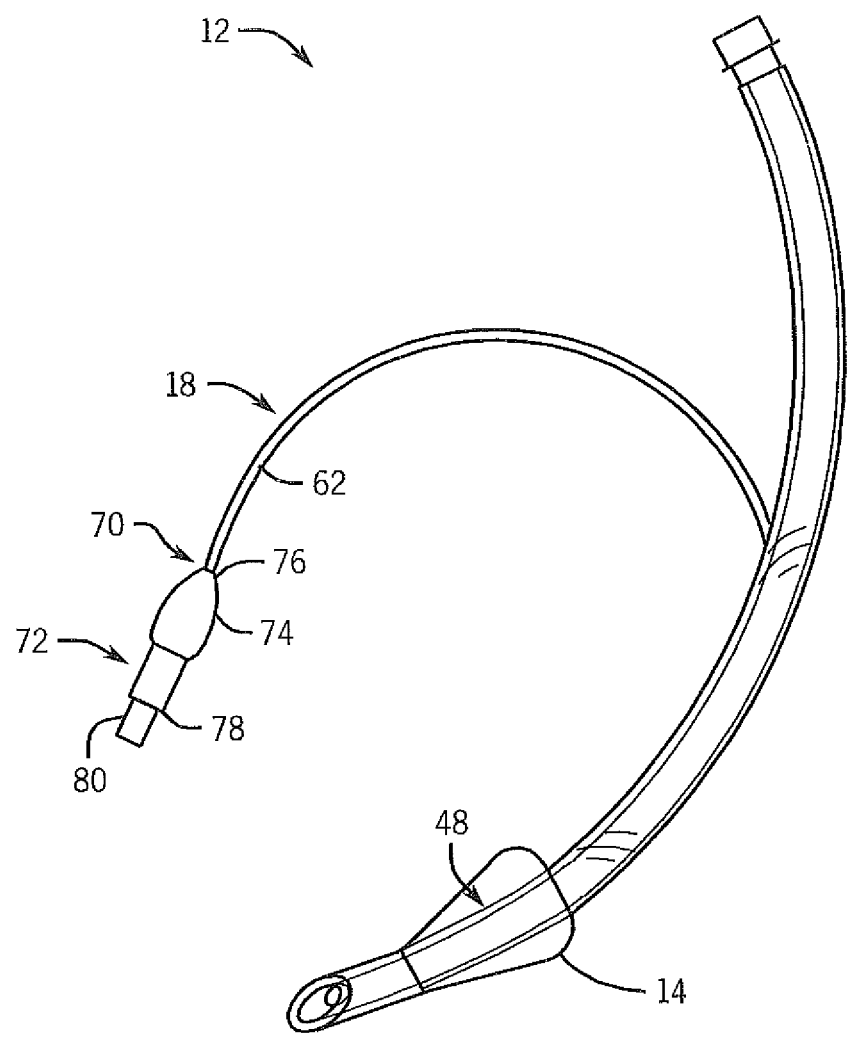
FIG. 3 is a perspective view of an endotracheal tube with a pilot balloon assembly including a pressure transducer that may be used in conjunction with the system of FIG. 1.

FIG. 3 illustrates a tracheal tube 12 including a pilot balloon assembly 72 at the proximal end 70 of the inflation line 18. In particular embodiments (see FIGS. 4-7), the pressure transducer 20 may be associated with the pilot balloon assembly 72, which may include a pilot balloon 74 configured to be in fluid communication with the interior space 48 of the cuff 14. The pilot balloon is coupled to the proximal end 70 of the inflation line at a distal pilot balloon end 76. In the depicted embodiment, the proximal pilot balloon end 78 is coupled to a valve 80. The valve 80 is configured to open to allow the transfer of fluid in or out of the inflation system to inflate or deflate the cuff 14. For example, the valve 80 may be configured to accommodate an inflation syringe. In one implementation, insertion of the syringe may depress a spring-loaded plunger, which opens the valve 80. Removal of the syringe allows the plunger to return to a closed configuration of the valve 80. It should be understood that other configurations of a valve may also be incorporated into the pilot balloon assembly 72.

Figure 4:
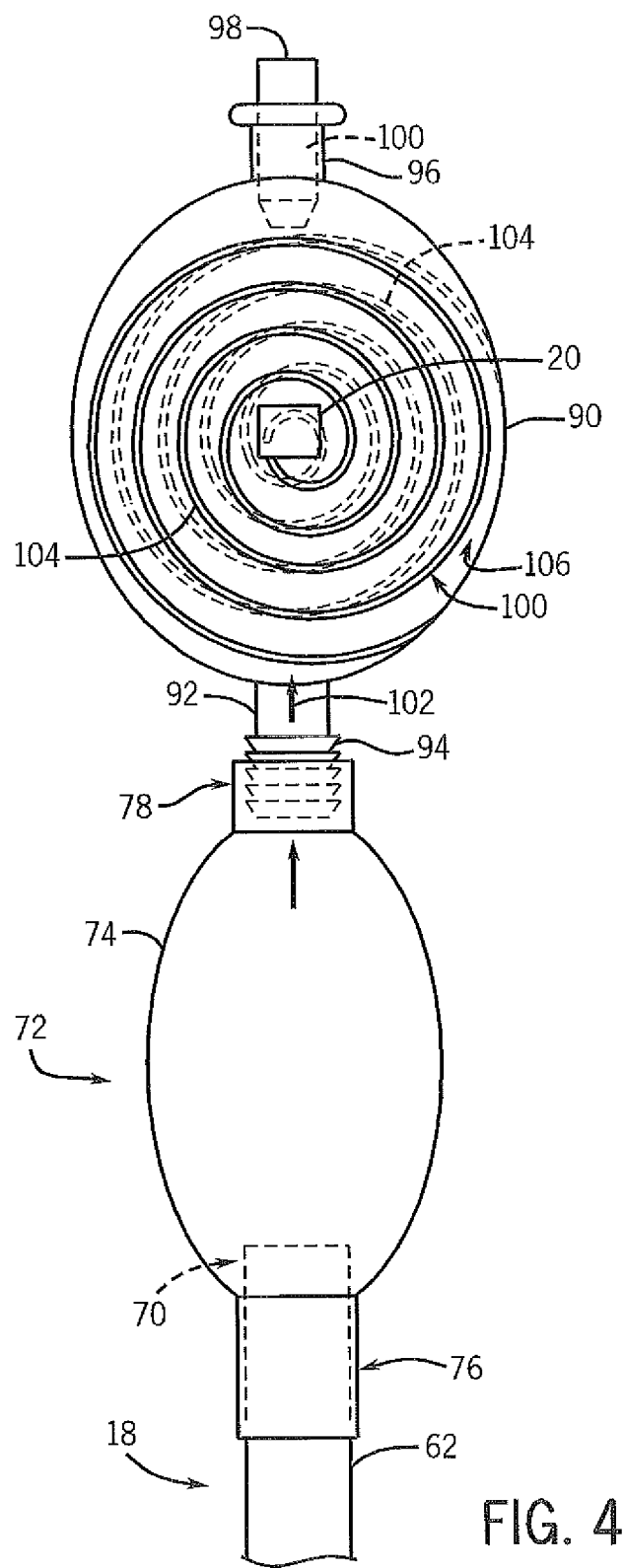
FIG. 4 is a perspective view of a pilot balloon assembly including a proximal adapter with a pressure transducer.

In certain embodiments, the pressure transducer 20 may be associated with an adapter assembly 90 configured to be inserted into opening formed in the pilot balloon 74 as shown in FIG. 4. In such an embodiment, a distal end 92 of the adapter assembly 90 may be configured to couple to an opening formed in the proximal pilot balloon end 78. A barb 94 or other retention feature may retain the adapter assembly 90 on the pilot balloon 74 through an interference fit with the proximal pilot balloon end 78. The adapter assembly 90 may be removable or, in embodiments, may be adhered to the pilot balloon 74. For example, in other embodiments, the adapter assembly 90 may be adhered to, welded, heat bonded, or overmolded to the pilot balloon assembly 72. A proximal opening 96 of the adapter assembly 90 is coupled to a valve 98. The valve 98 may operate in a manner similar to valve 80, allowing inflation or deflation of the cuff 14 via a syringe. Accordingly, a tube 12 with the adapter assembly 90 includes an integral cuff pressure transducer and is capable of cuff inflation via a syringe. The depicted arrangement may provide certain advantages over Y-type connectors that have separate branches to connect to a syringe and a pressure measurement device. By providing a single connection for a syringe (and no connection for a pressure transducer 20, which is integral to the adapter assembly 90), any confusion about which connector to use is eliminated. Further, the adapter assembly 90 may be used in conjunction with a standard pilot balloon 74 and inflation line 18, keeping the same capability of qualitative assessment of the cuff pressure by the clinician through squeezing the pilot balloon.

The adapter assembly 90 may define an enclosed space 100 that is in fluid communication with the interior of the pilot balloon 74 and may be formed from a rigid or conformable material that is substantially impermeable to ambient air. The adapter assembly 90 may be any suitable shape, such as generally spherical or elliptical. Because the cuff 14 may be inflated by transferring air from an inflation syringe (or other fluid source) through the interior enclosed space 100, the adapter assembly is not dead space or does not result in an overall loss of fluid from the cuff 14. Further, the inflation may be monitored via the pressure transducer 20 until a desired intracuff pressure is achieved. Fluid in the inflation system (represented by arrow 102) equilibrates to a constant pressure within the enclosed space 100, so that the measured pressure in the adapter assembly 90 represents the intracuff pressure.

The pressure transducer 20 may be coupled to the adapter assembly so that one surface is exposed to the ambient air and one surface is exposed to the enclosed space 100. The pressure transducer 20 may include a flexible membrane with an electrode surface. The interior pressure of the inflation system results in movement or deflection of the membrane and its electrode relative to a second electrode surface. The displacement generates an alternating signal that is related to the size of the gap between the electrode surface, the amount of displacement, and the thickness of the membrane. The pressure transducer 20 may be fabricated so that the displacement amount within expected cuff pressures is tuned to a particular frequency. The signal may be communicated via antennas 104. In the depicted arrangement, the antennas 104 are diametrically opposed to one another on an exterior surface of the adapter assembly 90. The pressure transducer 20 may be coupled to the antennas 104, which are configured to communicate with the patient monitor 30 in a selected band. The antennas 104 may be arranged with respect to the adapter assembly 90 to facilitate wireless communication at a desired distance or at multiple angles. For example, in one embodiment, one or more antennas 104 form a spiral or curved shape about the pressure transducer 20 and are disposed to increase overall surface coverage.

Figure 5:
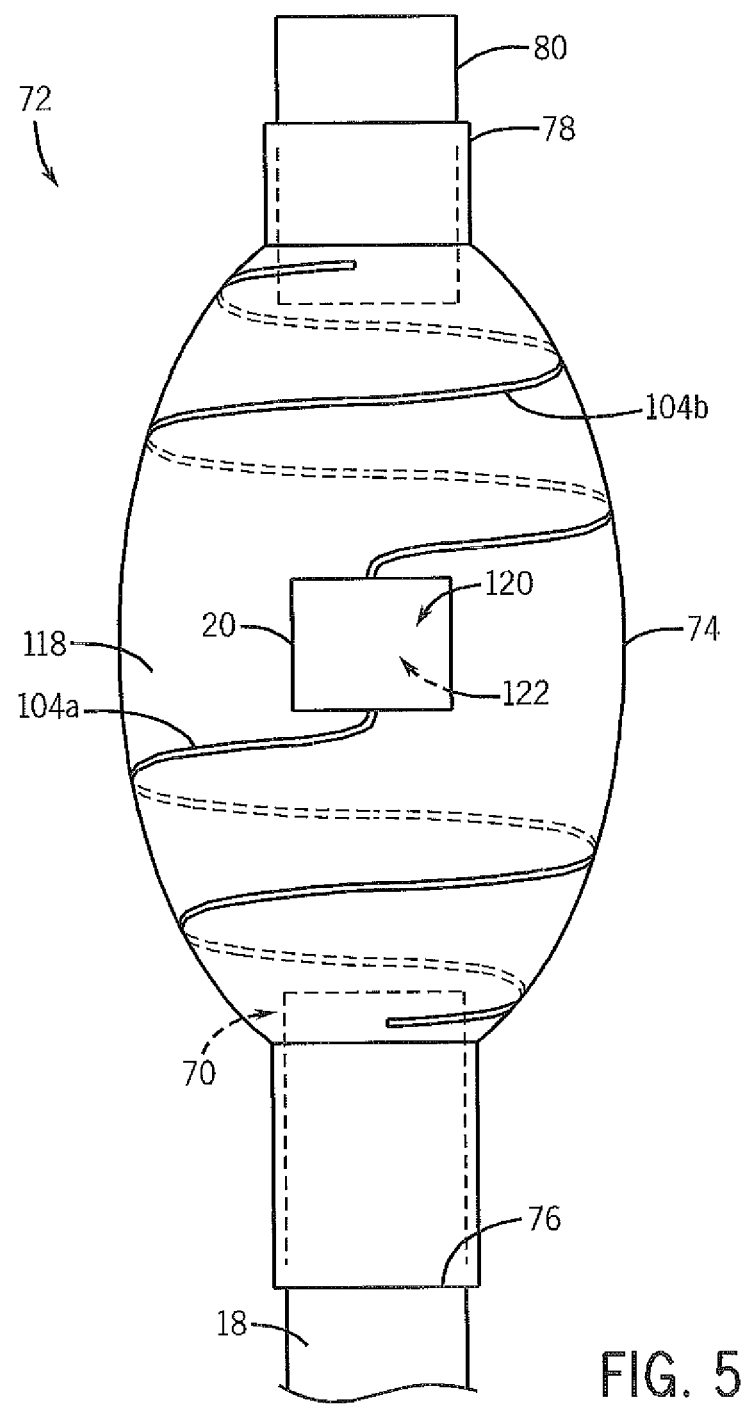
FIG. 5 is a perspective view of a pilot balloon assembly including a pressure transducer incorporated into a balloon wall.

In an alternate arrangement, the pressure transducer 20 may be coupled directly to the pilot balloon 74. As shown in FIG. 5, the pressure transducer 20 may be embedded in or otherwise formed within the pilot balloon wall 118. In one embodiment, the pilot balloon 74 may be manufactured with openings formed to connect at the distal pilot balloon end 76 to the inflation line and at the proximal pilot balloon end 78 to the valve 80. An opening in the balloon wall 118 may be cut to accommodate the pressure transducer 20, and the pressure transducer 20 may be positioned relative to the pilot balloon 74 such that the interior surface 120 is within the enclosed space of the pilot balloon and the exterior surface 122 is exposed to ambient air. Antennas 104a and 104b may be wrapped about the exterior of the pilot balloon walls 118.

Figure 6:
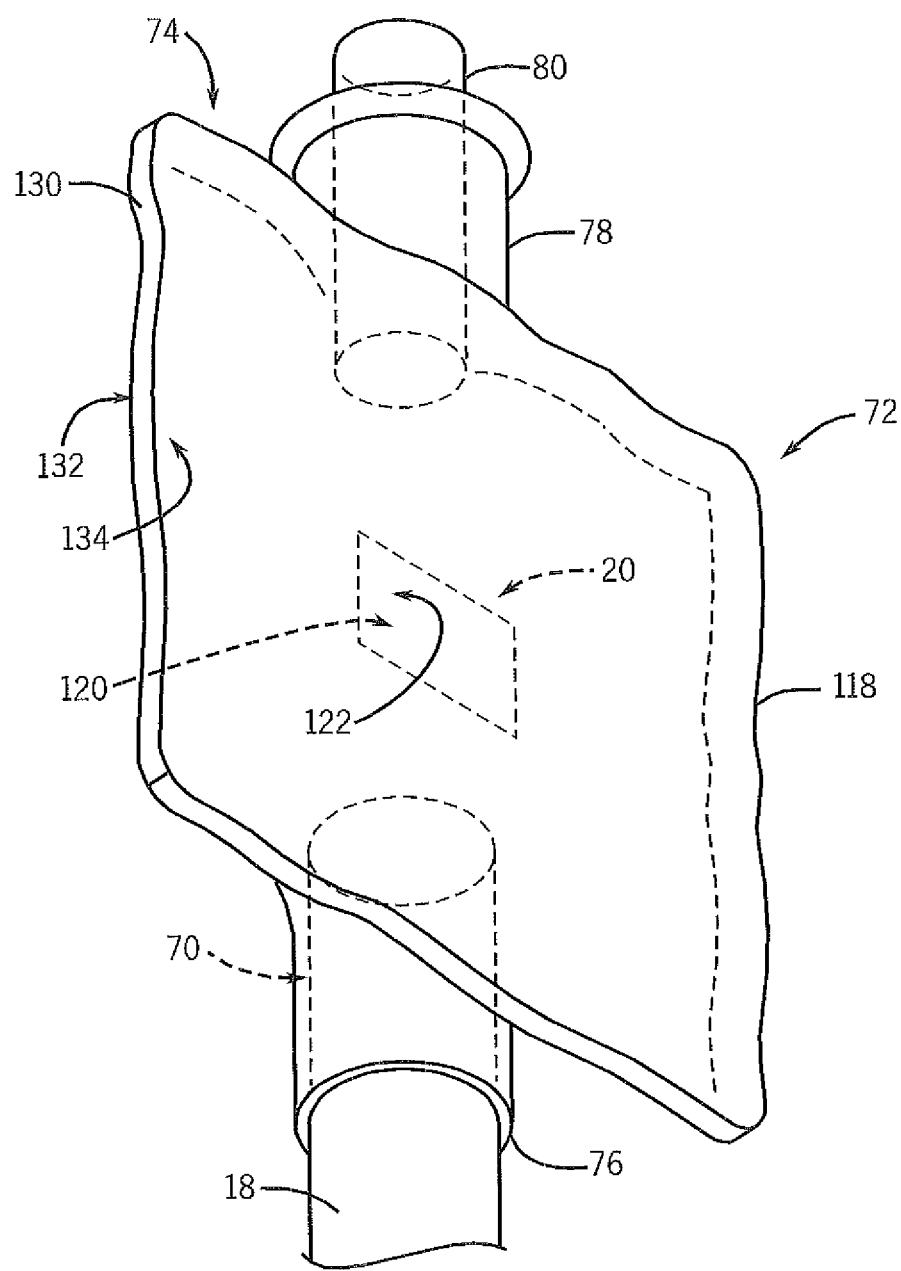
FIG. 6 is a perspective view of a pilot balloon assembly including a pressure transducer that forms a side of the pilot balloon.
Figure 7:
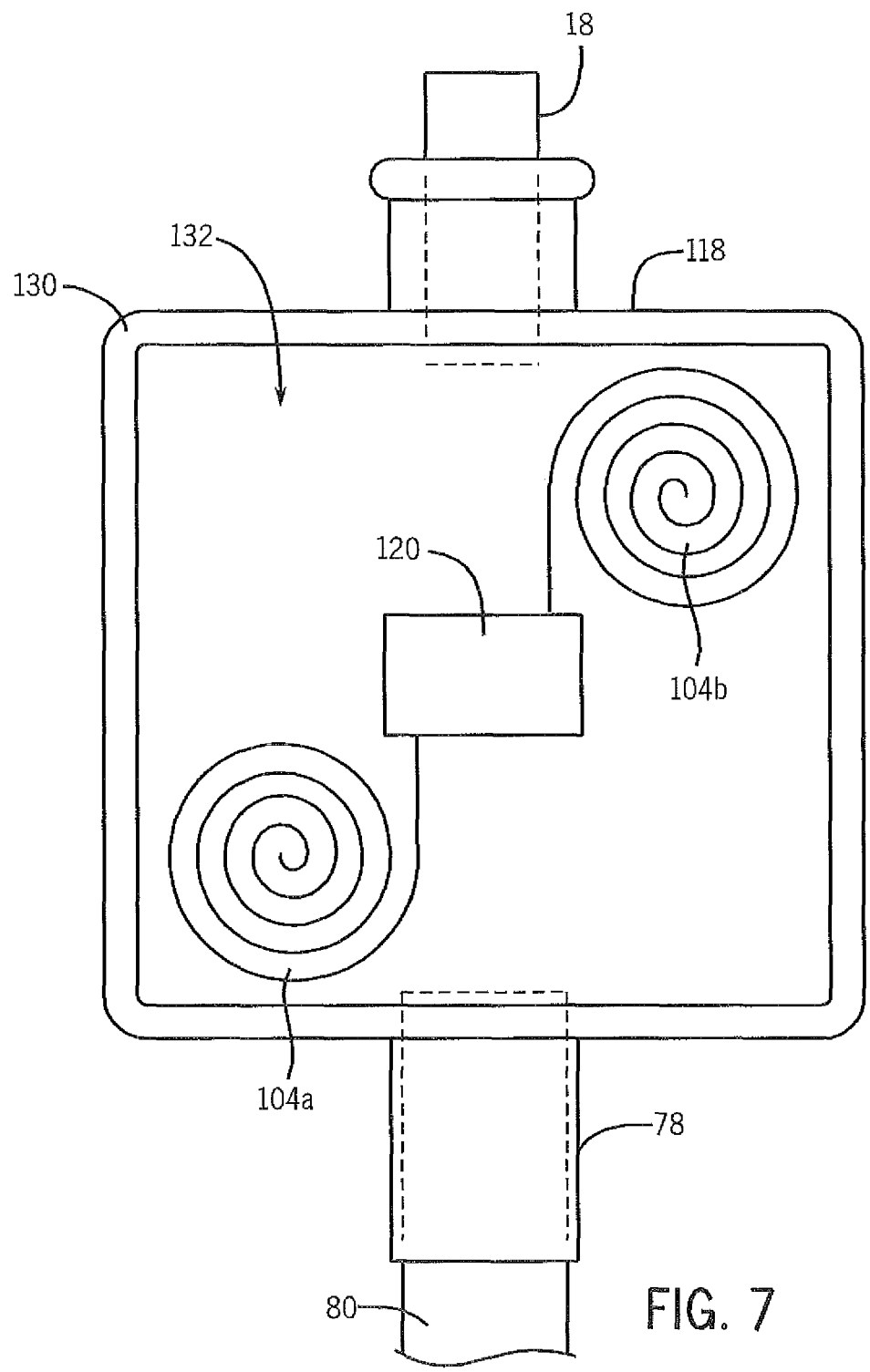
FIG. 7 is a side view of a pilot balloon assembly of FIG. 6.

FIG. 6 depicts an implementation in which the pressure transducer 20 is disposed on a substrate 130. The substrate 130 may be rigid or conformable. In embodiments in which the substrate is rigid, the balloon walls 118 remain conformable, which allows a clinician to feel the stiffness to estimate the cuff pressure. The substrate 130 may provide more surface area to attach to the balloon walls 118. For example, the balloon walls may be glued or otherwise adhered to an exterior surface 132 of the substrate (or, in alternative implementation, to an interior surface 134). In certain embodiments, the substrate 130 may be a two-part component that clips the balloon walls 118 to enclose the interior of the pilot balloon 74.

The substrate 130 may also provide a surface for one or more antennas 104. In the depicted arrangement, the antennas 104a and 104b (see FIG. 7) are offset from one another on the exterior surface 132 to avoid interference. In another embodiment, the antennas 104a and 104b may be arranged in concentric spirals about the pressure transducer 20.

Figure 8:
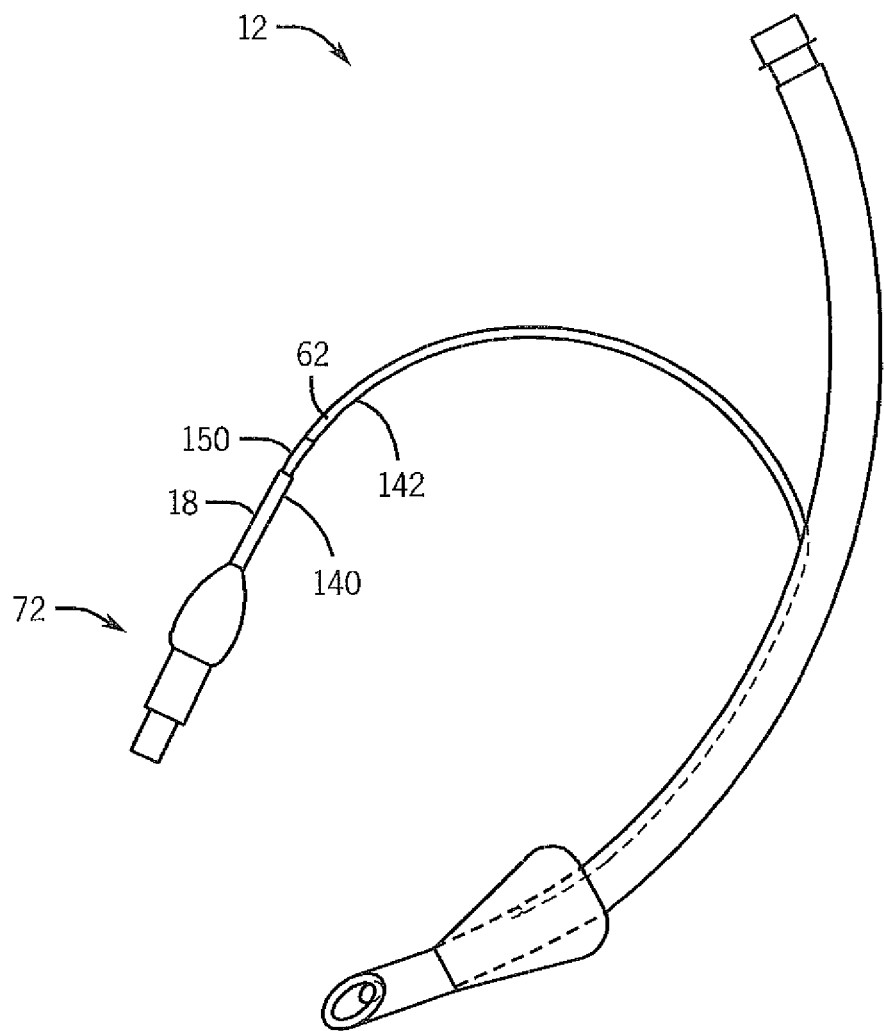
FIG. 8 is a perspective view of an endotracheal tube with an inflation line and an in-line adapter including pressure transducer that may be used in conjunction with the system of FIG. 1.

The pressure transducer 20 may also be associated with the inflation line 18. FIG. 8 is a perspective view of the tracheal tube 12 including an inflation line adapter 150 that is positioned in-line with the inflation line on the exterior portion 62. In such an arrangement, the pilot balloon assembly 72 may be formed according to conventional techniques. The inflation line adapter 150 connects or bridges a proximal portion 140 and a distal portion 142 of the inflation line 18. In one embodiment, the inflation line adapter 150 may be coupled to the inflation line 18 by cutting the inflation line 18 and inserting the inflation line adapter 150 between the two portions 140 and 142 that were previously adjacent to one another.

Figure 9:
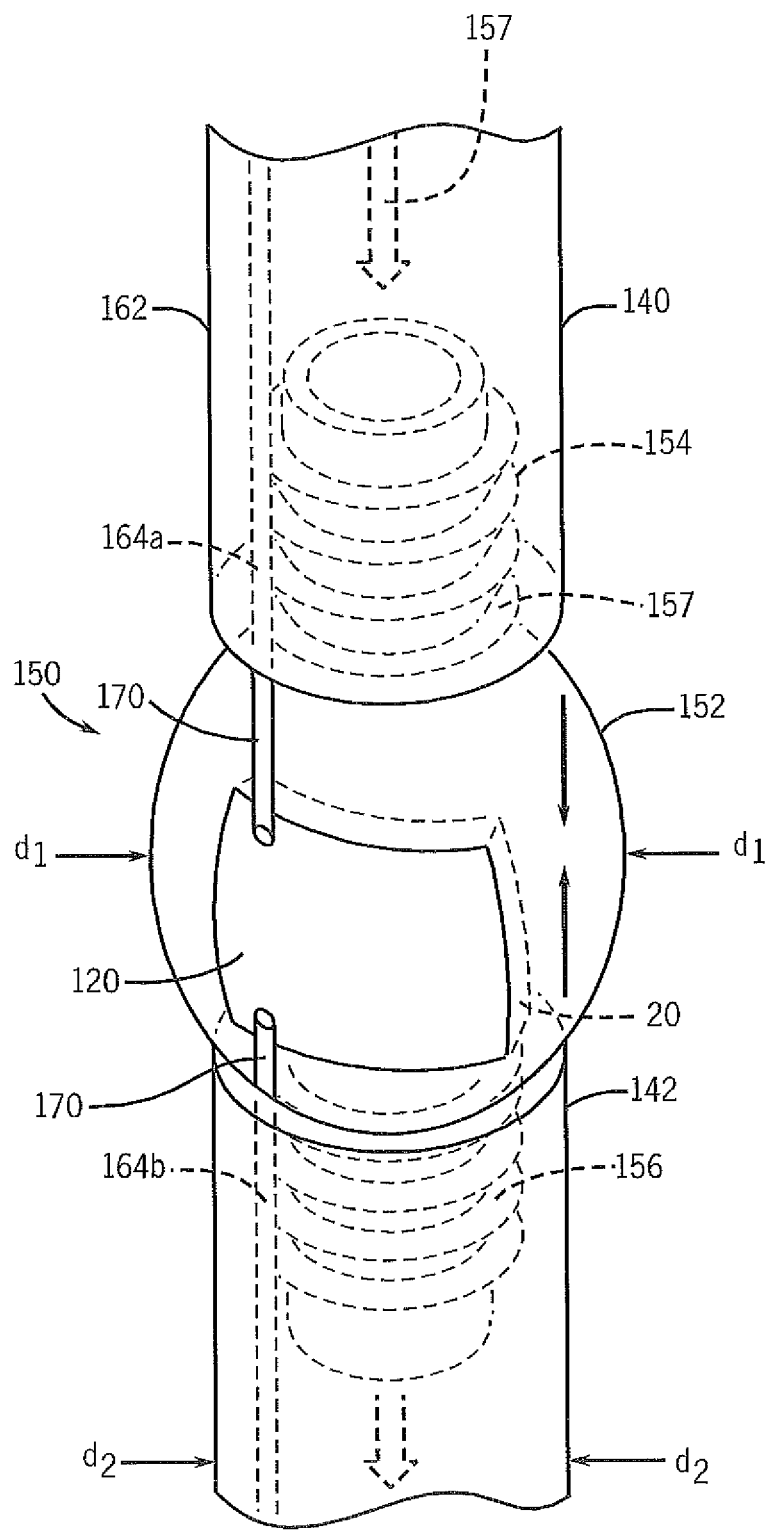
FIG. 9 is a side view of an example of an in-line adapter including a pressure transducer.

FIG. 9 is a side view of the inflation line adapter 150. The exterior surface 152 is sized and shaped to fit in-line with the portions 140 and 142. The exterior surface 152 may be generally barrel-shaped. In one embodiment, the exterior surface 152 defines a widest diameter d1 is at least wider than the outer diameter d2 of the inflation line. Such an arrangement prevents the proximal portion 140 and the distal portion 142 from being pushed towards one another to cover the exterior surface 120 of the pressure transducer 20. The inflation line adapter 150 may be retained in place via barbed ends 154 and 156 and/or adhered to the inflation line 18. For example, in other embodiments, the inflation line adapter 150 may be adhered to, welded, heat bonded, or overmolded to the inflation line 18. The barbed ends 154 and 156 are hollow so that fluid, represented by arrows 157, is capable of moving through an enclosed space 158 and into the inflation line 18.

The antenna wires 164a and 164b may be soldered or otherwise coupled to the pressure transducer 20 and may run along the length of the inflation line 18 to the pressure transducer 20 in any suitable manner. For example, the antenna wires 164 may be embedded (e.g., via extrusion) within the wall 162 of the tube inflation line 18, may be run along the inside or the outside of the inflation line 18, or may be printed on the inflation line 18. In one embodiment, the antenna wires 164 embedded within the wall 162 of the inflation line 18 are exposed by stripping away a portion of the inflation line wall 162 to reveal the wires 164, which are soldered to the pressure transducer 20 and the coupling 170 may be protected by epoxy.

In another embodiment, the pressure transducer 120 may be integrated into a wall of the inflation line 18 such that at least a portion of the pressure transducer 120 is exposed to ambient air and a portion of the pressure transducer 120 is exposed to the interior of the inflation line 18. The antenna wires 164 may soldered to the pressure transducer and the coupling may be protected with epoxy.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of cuff pressure, but these techniques may also be utilized for the measurement and/or analysis of the tracheal pressure based on measurements of cuff pressure. Rather, the various embodiments may cover all modifications, equivalents, and alternatives falling within the spirit and scope of the disclosure as defined by the following appended claims.

What is claimed is:

1. A tracheal tube comprising:
   a conduit configured to be inserted into a trachea of a subject;
   an inflatable cuff disposed on the conduit and configured to contact the trachea of the subject;
   an inflation line in fluid communication with the inflatable cuff comprising an exterior portion extending away from a wall of the conduit and a distal opening disposed in an interior space of the inflatable cuff;
   a pilot balloon associated with a proximal end of the inflation line on the exterior portion;
   an adapter positioned on the exterior portion of the inflation line and distally to the pilot balloon, wherein the adapter couples two sections of the inflation line in fluid communication with one another; and
   a pressure transducer positioned on a wall of the adapter comprising an interior surface exposed to fluid in the inflation line and an exterior surface exposed to ambient air.

2. The tracheal tube of claim 1, wherein the adapter comprises a memory circuit storing calibration data.

3. The tracheal tube of claim 1, comprising one or more antenna wires formed in a wall of the inflation line and coupled to the pressure transducer.

4. The tracheal tube of claim 3, wherein the one or more antenna wires comprise an end not coupled to the pressure transducer and that extends away from the adapter.

5. The tracheal tube of claim 3, wherein the pressure transducer is configured to communicate wirelessly with a patient monitor via the one or more antenna wires.

6. The tracheal tube of claim 1, wherein the adapter comprises a barrel shape.

7. The tracheal tube of claim 1, wherein an interior diameter of the adapter is equal to or less than an interior diameter of the two sections of the inflation line.

8. The tracheal tube of claim 1, wherein the adapter comprises barbed ends that are configured to retain the adapter between the two sections of the inflation line.

9. The tracheal tube of claim 1, wherein an exterior diameter of the adapter is greater than an exterior diameter of the two sections of the inflation line.

10. The tracheal tube of claim 1, wherein the pressure transducer comprises a membrane.

* * * * *